(12) United States Patent
Hino

(10) Patent No.: US 6,878,107 B2
(45) Date of Patent: Apr. 12, 2005

(54) END OF SIDE-LOOKING ENDOSCOPE

(75) Inventor: Kazuhiko Hino, Saitama (JP)

(73) Assignee: Fujinon Corporation, Saitama (JP)

( * ) Notice: Subject to any disclaimer, the term of this patent is extended or adjusted under 35 U.S.C. 154(b) by 0 days.

(21) Appl. No.: 10/686,664

(22) Filed: Oct. 17, 2003

(65) Prior Publication Data

US 2004/0082836 A1 Apr. 29, 2004

(30) Foreign Application Priority Data

Oct. 23, 2002 (JP) ........................................ 2002-308306
Oct. 23, 2002 (JP) ........................................ 2002-308307

(51) Int. Cl.[7] .............................................. A61B 1/00
(52) U.S. Cl. ....................... 600/122; 600/121; 600/170; 600/127; 600/129
(58) Field of Search ........................ 600/109, 121–122, 600/127, 129–130, 170

(56) References Cited

U.S. PATENT DOCUMENTS 5,860,913 A * 1/1999 Yamaya et al. ............. 600/127
5,865,726 A * 2/1999 Katsurada et al. .......... 600/127
5,868,663 A * 2/1999 Katsurada et al. .......... 600/107

FOREIGN PATENT DOCUMENTS

| JP | 8-76028 | 3/1996 |
| JP | 9-253036 | 9/1997 |

* cited by examiner

Primary Examiner—Linda C. M. Dvorak
Assistant Examiner—Michael Straightiff
(74) Attorney, Agent, or Firm—Young & Thompson (57) ABSTRACT

An end of a side-looking endoscope is constituted by covering an end body with a cap. The end body has a stand lever accommodation room in which a stand lever is accommodated, and a ridge is provided on a top surface of the stand lever accommodation room. A groove is formed inside the cap, and the groove is engaged with the ridge. The cap is thus prevented from dropping or rotating from the end body.

2 Claims, 6 Drawing Sheets

FIG.7

END OF SIDE-LOOKING ENDOSCOPE

BACKGROUND OF THE INVENTION

1. Field of the Invention

The present invention relates to an end of a side-looking endoscope, and in particular, to an end of a side-looking endoscope having a cap detachably affixed on an end body.

2. Description of the Related Art

A side-looking endoscope is intended to observe the inside of an observed body on a side of its end from an observation port on a side surface of its end and to lead various treatment devises such as forceps to the inside of the observed body on the side of its end via a treatment devise insertion channel provided inside so as to perform an incision, a biopsy, recovery of the contents and so on therewith.

An end of the endoscope has a metallic end body, and there is a problem that, if such an end body is in direct contact with mucous membranes of a patient, it may hurt them. For this reason, a cap made of rubber or the like for covering the end body is detachably affixed on the end body. The cap is formed by an elastic material, and has a circular minor diameter portion provided projectingly toward the inside on an inner radius surface close to its rear end. This minor diameter portion is fitted into a circumferential groove formed on a peripheral surface of the end body so as to lock the cap on the end body. There is a possibility that the cap may drop off the end body or rotate if forcefully passed through a narrowed area in the body during endoscopy. Japanese Patent Application Publication No. 9-253036 discloses that a detent member is affixed on the end body so that the rotation and drop of the cap is thereby prevented. This construction has, however, a problem that the detent member is a separate part from the end body, and also a problem that, if the detent member is formed as one with the end body, it is shaped astride a treatment devise insertion slot so that its structure and manufacturing become complicated.

An endoscope has an airtight optical system accommodation room provided inside the end body. An image-taking optical system such as a CCD and an illumination optical system such as a light guide are accommodated in this accommodation room. If the image-taking optical system and the illumination optical system are accommodated in separate rooms, each room becomes smaller so that workability deteriorates. Japanese Patent Application Publication No. 8-76028 discloses an endoscope accommodating the image-taking optical system and the illumination optical system in a common large optical system accommodation room. According to this endoscope, the accommodation room has such a wide frontage that it is easy to incorporate the image-taking optical system and the illumination optical system therein.

This construction, however, has a problem that its frontage is widened and so the airtight surface becomes too wide to be kept airtight. In particular, in the case where a metal sheet to be a lid of the accommodation room is adhered to the end body with an adhesive, there arises a problem that airtightness is reduced in conjunction with degradation of the adhesive. Furthermore, there is a problem that the metal sheet is exfoliated from the airtight surface of the end body by a springback to reduce the airtightness.

To prevent this, it is thinkable to fix the metal sheet with screws at a plurality of locations and thereby secure the airtightness. However, there is a problem that it is not possible to take enough space for screwing it at a plurality of locations due to high density of component members at the end of the endoscope, that is, the optical system accommodation room in particular.

SUMMARY OF THE INVENTION

The present invention has been implemented in consideration of such circumstances, and its object is to provide the end of a side-looking endoscope capable of keeping the airtightness of the accommodation room. Another object thereof is to provide the end of the side-looking endoscope of a simple structure capable of preventing the cap from dropping off the end body or rotating.

In order to attain the above-described object, the present invention is directed to an end of a side-looking endoscope, comprising: an end body which is provided at an end of an endoscope insertion portion, the end body having a stand accommodation groove and an optical system accommodation room, the optical system accommodation room being formed on a side of the stand accommodation groove and accommodating an image-taking optical system and an illumination optical system; a treatment devise stand which laterally guides an end of a treatment devise from the end body, the treatment devise stand being swingably supported within the stand accommodation groove; a cap which is detachably affixed on the end body to cover the end body; a protective covering which covers the optical system accommodation room, the protective covering having an engagement part for engaging with the end body, the protective covering being joined to the end body through the engagement part; and a sealing agent through which the protective covering is screw-connected to the end body on a joint surface of the end body.

According the present invention, the protective covering is joined to the end body by engaging it therewith so that the protective covering is securely kept in a state of being joined to the end body. Therefore, it is possible, by applying the sealing agent on the joint surface, to securely seal the joint surface so as to keep the airtightness of the optical system accommodation room. Moreover, it is possible, by engaging the protective covering to the end body, to render the number of screw cramps minimum. Therefore, the space required for the screw cramps becomes smaller so that the end can be of a smaller diameter.

Preferably, the protective covering is joined to the end body by engaging motion and sliding motion. According to the present invention, work for joining the protective covering to the end body becomes more secure so as to keep the airtightness of the optical system accommodation room more securely.

In order to attain the above-described object, the present invention is also directed to an end of a side-looking endoscope, comprising: an end body which is provided at an end of an endoscope insertion portion, the end body having a stand accommodation groove and a stand lever accommodation room, the stand lever accommodation room being formed on a side of the stand accommodation groove; a treatment devise stand which laterally guides an end of a treatment devise from the end body, the treatment devise stand being swingably supported within the stand accommodation groove; a stand lever which is linked to the treatment devise stand, the stand lever being arranged in the stand lever accommodation room; and a cap which is detachably affixed on the end body to cover the end body, wherein an engagement part between the end body and the cap is formed by an upper portion of the stand lever accommodation room and an inside of the cap.

The present inventor paid attention to existence of a dead space on the stand lever accommodation room, and utilized the dead space to prevent the cap from dropping and rotating. Here, upper means an observation side.

According to the present invention, it is possible, by engaging the upper portion of the stand lever accommodation room of the end body with the inside of the cap, to prevent the cap from dropping and rotating from the end body. In particular, the engagement part is provided to the portion which was the dead space so that a detent can be easily performed without enlarging the diameter of the end. The engagement part is provided in the upper portion of the stand lever accommodation room so as to prevent the cap from riding up from a rim of the stand accommodation groove.

Preferably, the engagement part comprises a projection formed in the upper portion of the stand lever accommodation room and a recess formed inside the cap.

Preferably, the projection in the upper portion of the stand lever accommodation room is continuously formed as a ridge in an inserting direction of the cap. According to the present invention, the cap can be affixed easily with the projection as a guide for inserting the cap into the end body. The portion forming the recess of this cap forms a part of an inductive wall of the treatment devise.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein.

DETAILED DESCRIPTION OF THE PREFERRED EMBODIMENTS

Hereafter, preferred embodiments of an end of a side-looking endoscope according to the present invention will be described in detail by referring to the attached drawings.

Figure 1:
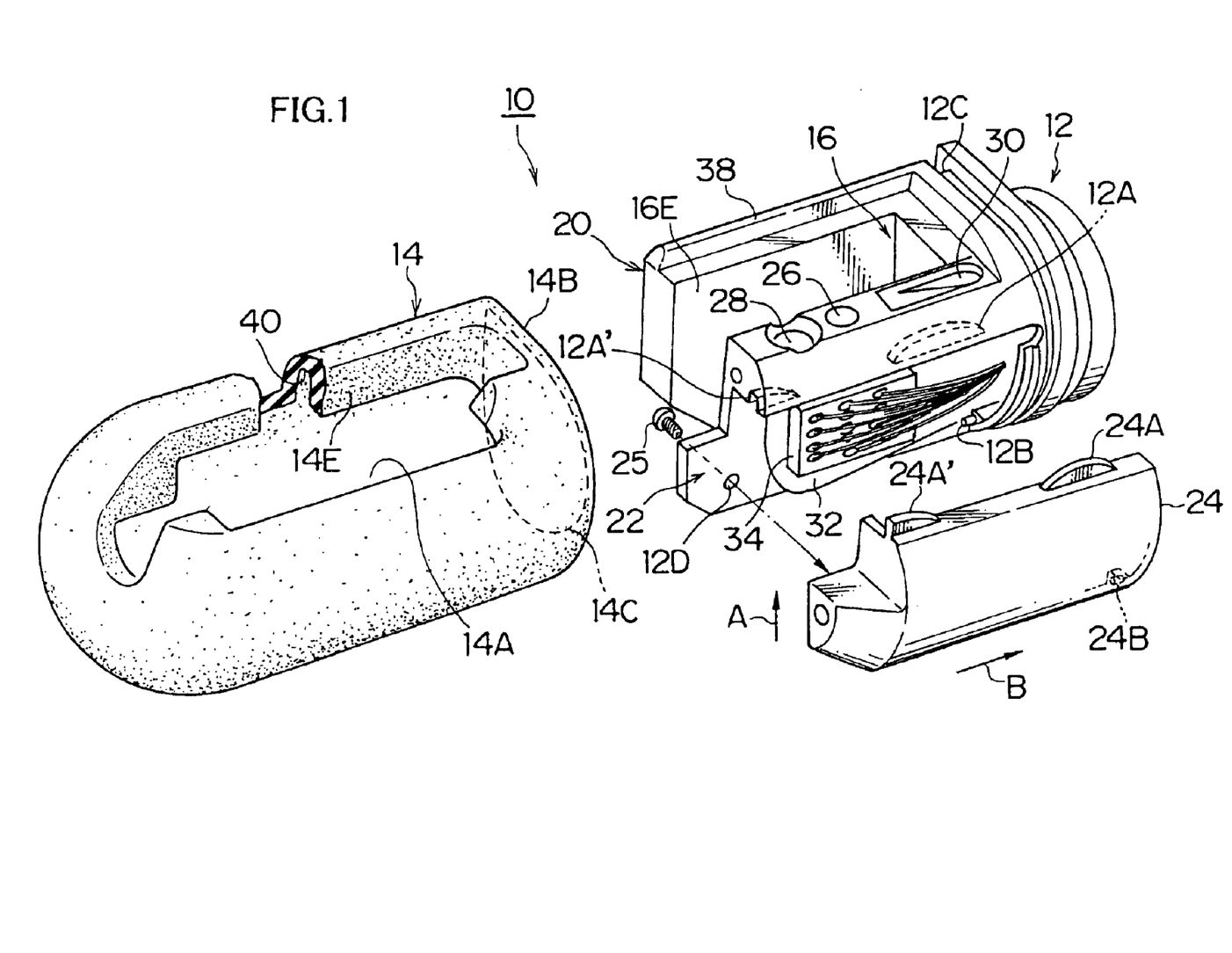
FIG. 1 is an assembly drawing showing structure of an end of a side-looking endoscope according to the present invention.

FIG. 1 is an exploded perspective view showing structure of an end 10 of the side-looking endoscope according to an embodiment of the present invention.

As shown in FIG. 1, the end 10 has a cap 14 for covering an end body 12. The cap 14 is made of an elastic material such as silicone rubber, and an opening 14A is formed on a top surface thereof. A base terminal 14B of the cap 14 has a minor diameter portion 14C of which inside diameter is small provided thereto, and the minor diameter portion 14C is engaged with a groove 12C of the end body 12. Thus, the cap 14 is mounted on the end body 12.

The end body 12 is made of a corrosion-resistant metal such as stainless steel. At a central position of the end body 12, a stand accommodation groove 16 for accommodating a stand 46 mentioned later (refer to FIGS. 6 and 7) is formed, and a treatment devise insertion channel 18 (refer to FIG. 2) is communicated with the stand accommodation groove 16. The treatment devise insertion channel 18 is connected to a manual control portion by being inserted into an endoscope insertion portion (not shown). Thus, on inserting the treatment devise into the treatment devise insertion channel 18 from the manual control portion, the treatment devise is guided to the stand accommodation groove 16. The guided treatment devise is stood up by the stand 46 and is led upward.

A stand lever accommodation room 20 is provided on the side of the stand accommodation groove 16. A stand lever 44 mentioned later (refer to FIGS. 6 and 7) for swinging the stand 46 is accommodated inside the stand lever accommodation room 20. An optical system accommodation room 22 is provided on the opposite side of the stand lever accommodation room 20 sandwiching the stand accommodation groove 16.

Figure 2:
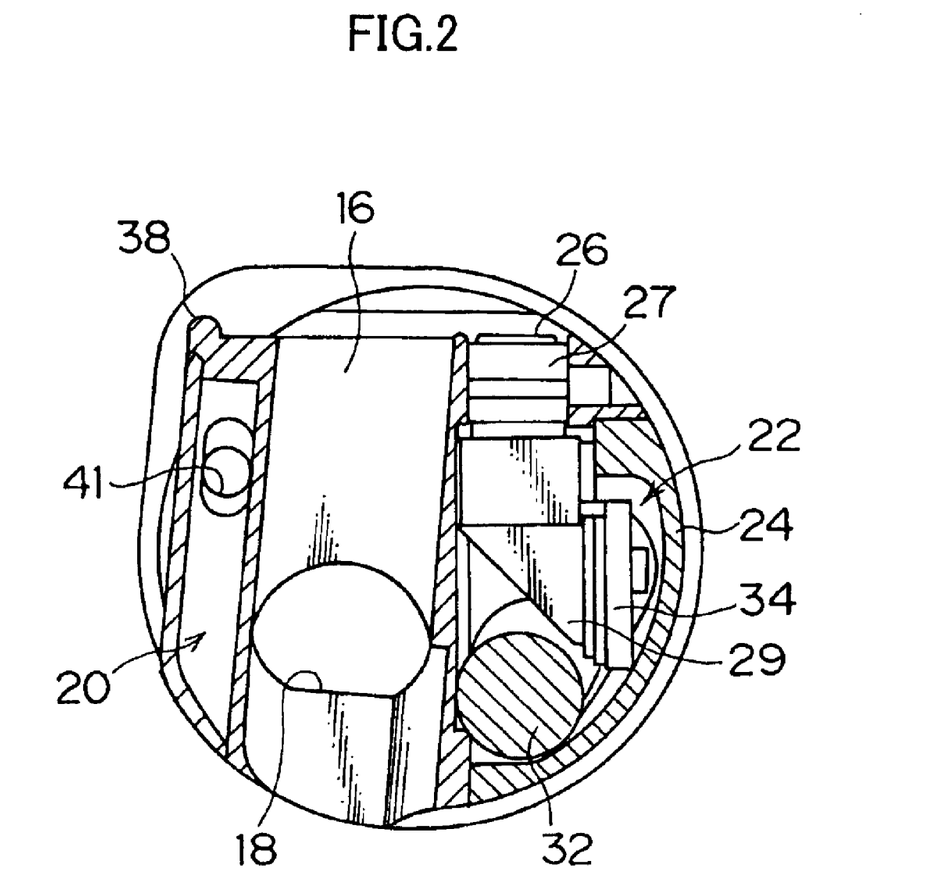
FIG. 2 is a front sectional view of an end body.
Figure 3:
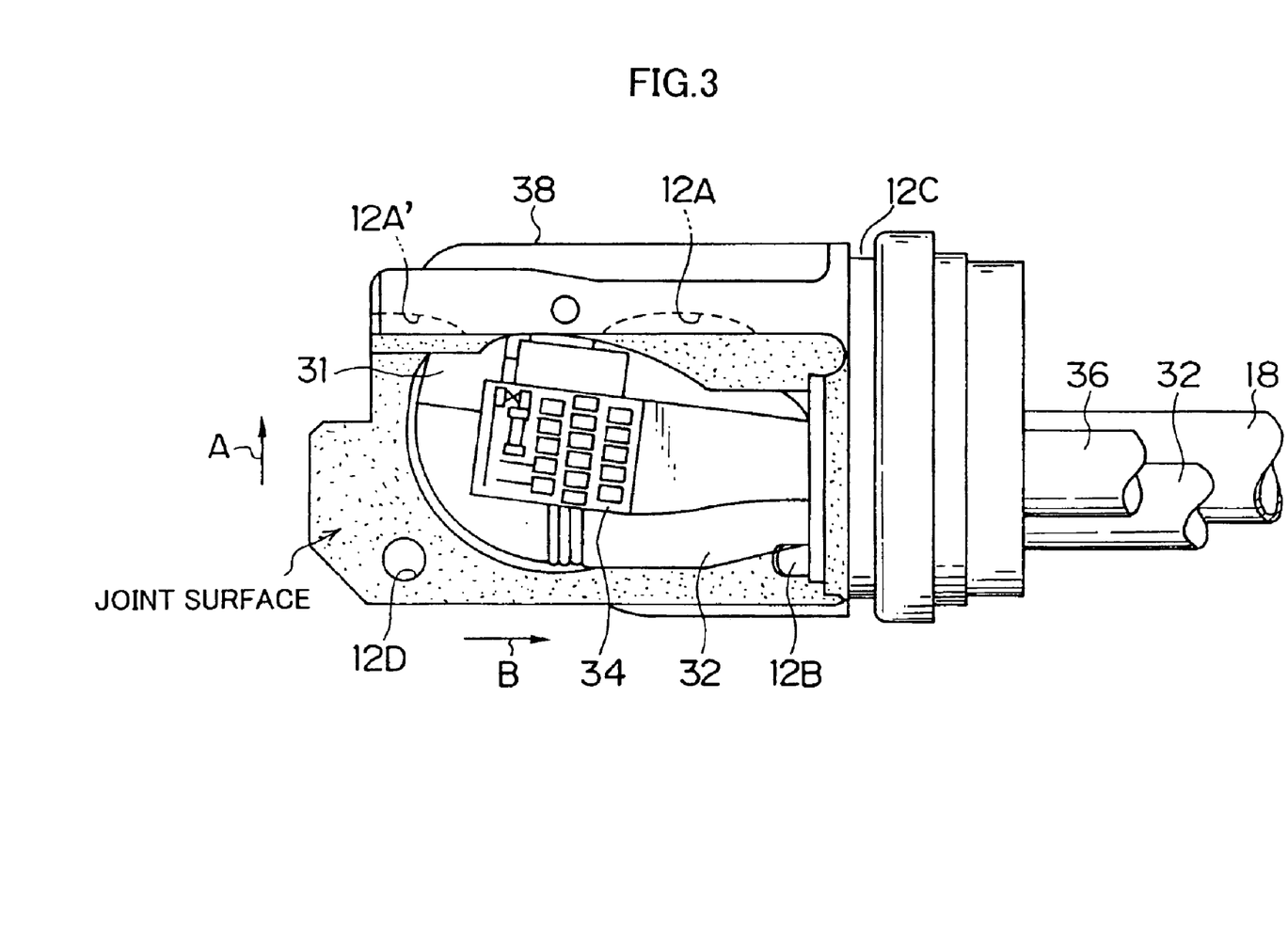
FIG. 3 is a side view showing an optical system accommodation room of which protective covering is removed.
Figure 4:
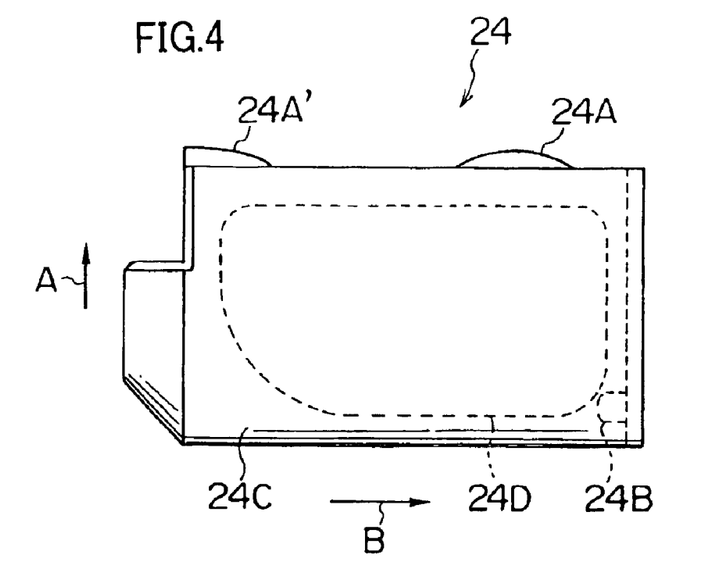
FIG. 4 is a side view of the protective covering.
Figure 5:
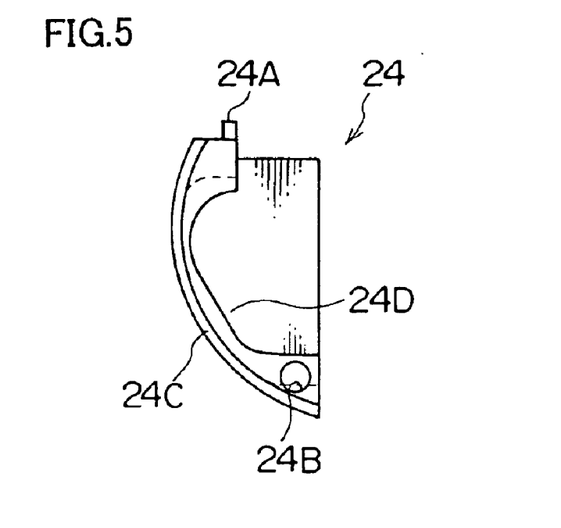
FIG. 5 is a right side view of the protective covering in FIG. 4.

FIG. 2 is a cross-sectional view of the end body 12, and FIG. 3 is a side view of the end body 12 having a protective covering 24 removed therefrom and exposing the optical system accommodation room 22. FIGS. 4 and 5 show the protective covering 24.

The protective covering 24 is created by a cutting process, where its outer surface 24C is formed like an arc and a dent 24D is provided inside as shown in FIGS. 4 and 5. Therefore, the hollow optical system accommodation room 22 is formed by affixing the protective covering 24 to the end body 12 shown in FIG. 3.

Arc-shaped engagement projections 24A and 24A' are formed on a top edge of the protective covering 24. The end body 12 has engagement grooves 12A and 12A' for having the engagement projections 24A and 24A' engaged therewith from the direction of the arrow A formed thereon. The engagement groove 12A is formed to be longer in the direction of the arrow B than the engagement projection 24A, and the engagement groove 12A' is connecting to the end surface. Therefore, it is possible to slightly slide the protective covering 24 in the direction of the arrow B in the state of having the engagement projections 24A and 24A' engaged with the engagement grooves 12A and 12A'.

The end body 12 has an engagement pin 12B provided in an extended condition thereon. The protective covering 24 has an engagement hole 24B formed for having the engagement pin 12B inserted therein and engaged therewith. The engagement pin 12B is engaged with the engagement hole 24B by sliding the protective covering 24 in the direction of the arrow B in the state of having the engagement projection 24A engaged with the engagement groove 12A.

The protective covering 24 engaged with the end body 12 is fixed by a screw 25 shown in FIG. 1. The screw 25 is inserted into a hole 12D formed on the end body 12, and is tightened up into a screw hole (not shown) formed inside the protective covering 24. Thus, the protective covering 24 is fixed in a state in which its edges are joined to the end body 12 throughout the circumference. A sealing agent is applied to the joint surface of the protective covering 24 and the end body 12 (refer to FIG. 3). Thus, a clearance between the protective covering 24 and the end body 12 is sealed so that the optical system accommodation room 22 is kept airtight.

As shown in FIG. 1, in the upper portion of the optical system accommodation room 22, an observation window 26 and an irradiation window 28 are placed facing the side of the end 10, and an air/water supply opening 30 facing the observation window 26 is provided. The air/water supply opening 30 is connected to an external device via an air/water supply tube (not shown) inserted into the endoscope insertion portion, and an air/water supply button on the manual control portion is operated to emit compressed air or water from the air/water supply opening 30 to the observation window 26 so as to cleanse the observation window 26. The observation window 26, irradiation window 28 and air/water supply opening 30 are provided at the positions facing the opening 14A of the cap 14 on covering the end body 12 with the cap 14. Hereafter, the surface on which the observation window 26 is placed is referred to as a top surface, and an observation direction observed from the observation window 26 is referred to as an upward direction.

The image-taking optical system and the illumination optical system are accommodated inside the optical system accommodation room 22. The illumination optical system has an illumination lens optical system 31 placed inside the irradiation window 28 shown in FIG. 3 and a light guide 32 placed with its end facing the illumination lens optical system 31. The light guide 32 is inserted into the endoscope insertion portion, and its base terminal portion is connected to a light source device (not shown). Thus, irradiated light from the light source device is conveyed via the light guide 32, and is irradiated upward from the irradiation window 28.

The image-taking optical system has an objective lens optical system placed inside the observation window 26 and a CCD unit 34 placed behind the objective lens optical system via a prism, and the CCD unit 34 is connected to the external device (a processor for instance) via a cable 36. An object image taken in from the observation window 26 is converted into an electrical signal by image-taking optical system, and is conveyed to the external device so as to display the object image on a monitor thereof.

Figure 6:
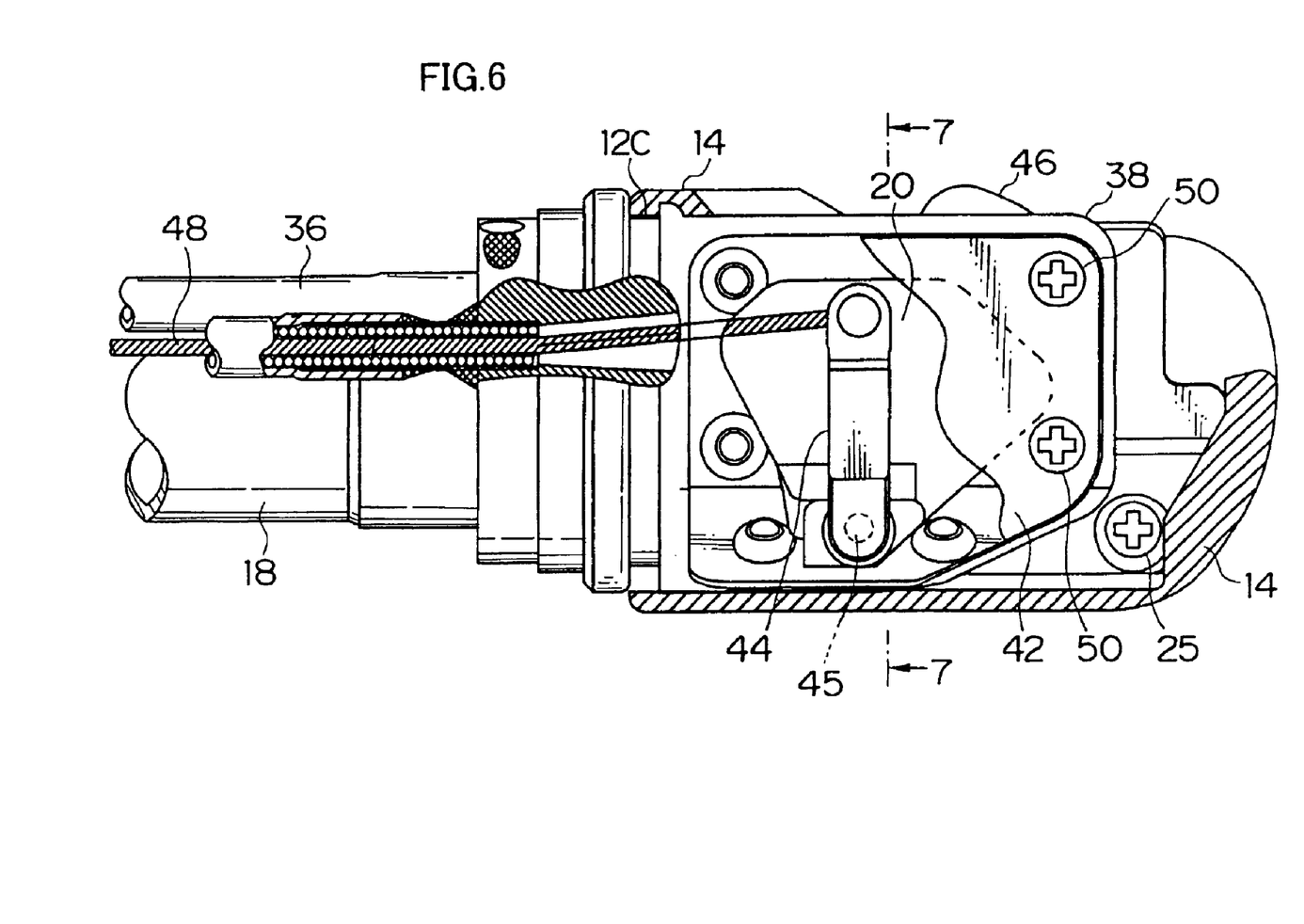
FIG. 6 is a longitudinal section of the end.
Figure 7:
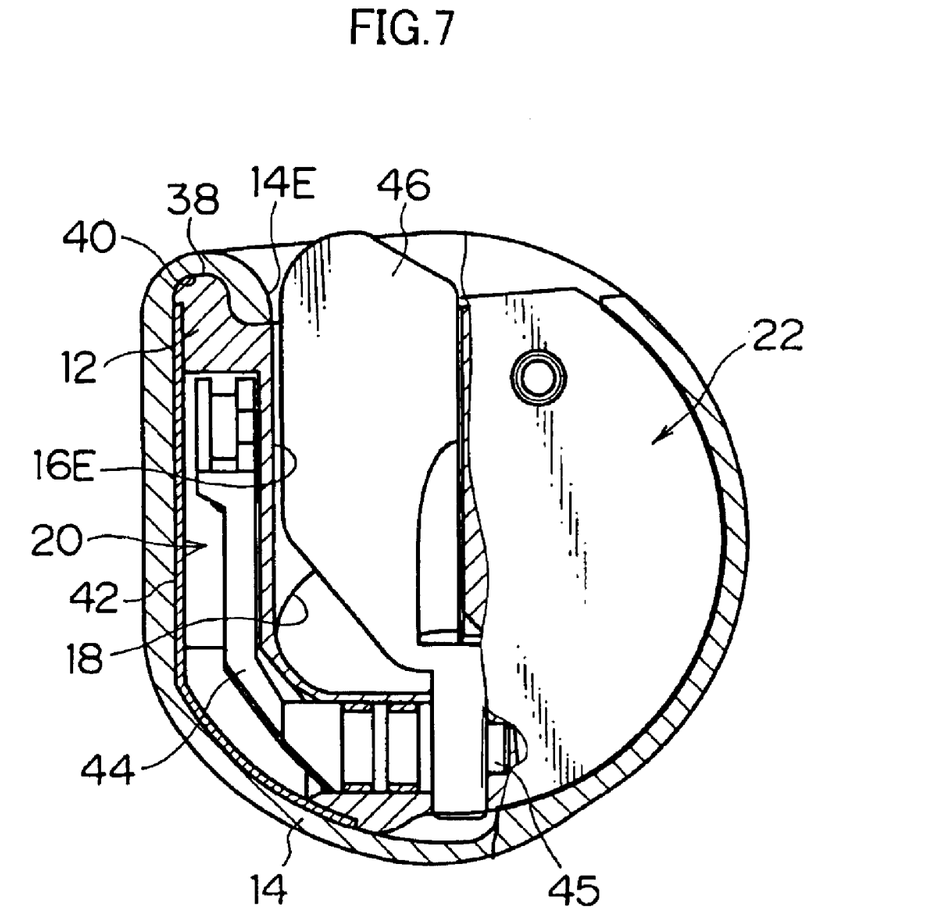
FIG. 7 is a cross-sectional view of the end.

The stand lever accommodation room 20 is closed by covering the end body 12 with a protection plate 42 as shown in FIGS. 6 and 7. The protection plate 42 is fixed on the end body 12 with screws 50 at several locations, and the sealing agent is filled in the clearance between the protection plate 42 and the end body 12. Thus, the stand lever accommodation room 20 is kept airtight. The stand lever 44 is provided inside the stand lever accommodation room 20. The stand lever 44 has its lower end coupled to the stand 46 via an axis 45 so as to swing as one with the stand 46. The stand lever 44 has a stand wire 48 connected to its upper end, and the stand wire 48 is inserted into the endoscope insertion portion and then connected to the manual control portion. Therefore, on operating the manual control portion, the stand wire 48 is swung by being pushed and pulled so as to consequently swing the stand 46.

A ridge 38 is formed on the top surface of the stand lever accommodation room 20. The ridge 38 is formed in the longitudinal direction of the end 10 as shown in FIG. 1. A groove 40 (refer to FIG. 1) is formed inside the cap 14, that is, at the position corresponding to the ridge 38. The ridge 38 is engaged with the groove 40 on affixing the cap 14 on the end body 12. In that case, they are constituted so that a sidewall 16E of the stand accommodation groove 16 of the end body 12 and a sidewall 14E of the cap 14 are on the same surface. Thus, the sidewall 14E of the cap 14 operates as an inductive wall of the treatment devises so as to prevent the treatment devise stood up by the stand 46 from falling onto the stand lever accommodation room 20 side. The shape of the stand 46 is not limited to the one shown in FIGS. 6 and 7, but it is also possible, for instance, to vertically form a groove at the center of the stand 46 so as to guide the treatment devise with that groove.

Next, the operation of the end 10 constituted as above will be described.

The protective covering 24 will be affixed as follows.

First, the sealing agent is applied to the joint surface of the protective covering 24 and the end body 12. Next, the protective covering 24 is moved in the direction of the arrow A in FIG. 1, and the engagement projections 24A and 24A' are inserted into the engagement grooves 12A and 12A' of the end body 12 to be engaged therewith. In that case, they are engaged by slightly deviating the engagement projections 24A and 24A' to the end side.

Next, the protective covering 24 is slid in the direction of the arrow B to insert the engagement pin 12B into the engagement hole 24B. Thus, the protective covering 24 is joined to the end body 12, and the joint surface between the protective covering 24 and the end body 12 is sealed with the sealing agent so that the optical system accommodation room 22 is kept airtight.

The protective covering 24 engaged with the end body 12 is fixed on the end body 12 by inserting the screw 25 into the hole 12D of the end body 12 from the stand accommodation groove 16 side and tightening it up into the screw hole (not shown) of the protective covering 24.

The protective covering 24 thus fixed is screwed shut in the state of being engaged with the end body 12, and so it is securely joined to the end body 12. In particular, according to the present embodiment, the protective covering 24 is moved in the direction of the arrow A and then slid in the direction of the arrow B to be engaged with the end body 12 so that the joint work becomes secure. Therefore, it is possible, according to the present embodiment, to keep the optical system accommodation room 22 airtight just by applying the sealing agent to the joint surface.

According to the present embodiment, the engagement groove 12A is formed to be longer than the engagement projection 24A, and the engagement groove 12A' is formed while connecting to the end surface. Therefore, it is easy to perform the work for engaging the engagement projections 24A and 24A' with the engagement grooves 12A and 12A' and the work for sliding in the direction of the arrow B.

According to the present embodiment, the protective covering 24 is engaged with the end body 12, and so the number of screwed-shut locations can be reduced. To be more precise, it is possible to fix the protective covering 24 on the end body 12 with one screwed-shut location. Therefore, it is possible to effectively utilize the space compared to the case of providing a plurality of screwed-shut locations so that the end can be rendered thinner.

Furthermore, according to the present embodiment, the image-taking optical system and the illumination optical system are accommodated in the optical system accommodation room 22 in common so that the frontage of the optical system accommodation room 22 can be wide. Therefore, it is easy to perform assembly work of the image-taking optical system and the illumination optical system.

If the cap 14 is mounted on the end body 12 according to the present embodiment, the minor diameter portion 14C of the cap 14 is engaged with a groove 12C of the end body 12. At the same time, the ridge 38 of the end body 12 is engaged with the groove 40 of the cap 14 on affixing the cap 14 on the end body 12. The ridge 38 is engaged with the groove 40, and the cap 14 is thereby prevented from rotating, dropping and riding up from the end body 12. Therefore, it is possible, according to the present embodiment, to prevent the cap 14 from rotating, dropping and riding up. In particular, it is possible, according to the present embodiment, to prevent the cap 14 from riding up by having the treatment devise hooked by the lower end of the sidewall 14E of the cap 14.

According to the present embodiment, as the ridge 38 is provided on the stand lever accommodation room 20 which was a dead space in the past, and so it is possible to prevent the cap 14 from rotating without enlarging an outer diameter of the end 10.

According to the present embodiment, it is a simple structure in which the ridge 38 is provided to the end body 12 and the groove 40 is provided to the cap 14. Therefore, it requires neither another member as the detent nor complicated working of the end body 12.

Furthermore, the ridge 38 and the groove 40 are formed in the engagement direction of the cap 14 so that the ridge 38 and the groove 40 become guides on engaging the cap 14 with the end body 12 so as to improve the workability.

The shape of the engagement portion of the end body 12 and the cap 14 is not limited to the continuous ridge 38 and groove 40, but may be the projection and recess of an independent circle.

According to the above-mentioned embodiment, the projection is provided on the end body 12 side and the recess is provided on the cap 14 side to have them engaged. However, it is also possible to provide the recess on the end body 12 side and provide the projection on the cap 14 side to have them engaged.

Furthermore, the present invention is applicable to any airtight accommodation room provided inside the end 10. For instance, it is applicable to the stand lever accommodation room 20.

As described above, according to the end of the side-looking endoscope related to the present invention, the protective covering is engaged with the end body to be screwed-shut. Therefore, the joint condition between the protective covering and the end body is constantly maintained so as to securely keep the optical system accommodation room airtight. According to the present invention, the projection is provided on the stand lever accommodation room of the end body and the recess is provided inside the cap to be engaged with the projection so that the cap is prevented from rotating, or dropping from the end body.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An end of a side-looking endoscope, comprising:

an end body which is provided at an end of an endoscope insertion portion, the end body having a stand accommodation groove and an optical system accommodation room, the optical system accommodation room being formed on a side of the stand accommodation groove and accommodating an image-taking optical system and an illumination optical system;

a treatment devise stand which laterally guides an end of a treatment devise from the end body, the treatment devise stand being swingably supported within the stand accommodation groove;

a cap which is detachably affixed on the end body to cover the end body;

a protective covering which covers the optical system accommodation room, the protective covering having an engagement part for engaging with the end body, the protective covering being joined to the end body through the engagement part; and a sealing agent through which the protective covering is screw-connected to the end body on a joint surface of the end body.

2. The end of the side-looking endoscope as defined in claim 1, wherein the protective covering is joined to the end body by engaging motion and sliding motion.

* * * * *